United States Patent
Mukai et al.

(10) Patent No.: US 11,065,185 B2
(45) Date of Patent: *Jul. 20, 2021

(54) HAIR COLORING METHOD

(71) Applicant: SUNNYPLACE CO., LTD., Taito-ku (JP)

(72) Inventors: Nobuhito Mukai, Kuramae (JP); Takashi Mukai, Kuramae (JP)

(73) Assignee: SUNNYPLACE CO., LTD., Taito-ku (JP)

(*) Notice: Subject to any disclaimer, the term of this patent is extended or adjusted under 35 U.S.C. 154(b) by 0 days.

This patent is subject to a terminal disclaimer.

(21) Appl. No.: 16/962,750

(22) PCT Filed: Dec. 18, 2018

(86) PCT No.: PCT/JP2018/046659
§ 371 (c)(1),
(2) Date: Jul. 16, 2020

(87) PCT Pub. No.: WO2019/155769
PCT Pub. Date: Aug. 15, 2019

(65) Prior Publication Data
US 2020/0337958 A1    Oct. 29, 2020

(30) Foreign Application Priority Data

Feb. 8, 2018  (JP) .............................. JP2018-020935

(51) Int. Cl.
| | | |
|---|---|---|
| *A61Q 5/10* | (2006.01) |
| *A61K 8/22* | (2006.01) |
| *A61K 8/34* | (2006.01) |
| *A61K 8/44* | (2006.01) |
| *A61K 8/49* | (2006.01) |

(52) U.S. Cl.
CPC ................. *A61K 8/22* (2013.01); *A61K 8/34* (2013.01); *A61K 8/447* (2013.01); *A61K 8/4946* (2013.01); *A61Q 5/10* (2013.01); *A61K 2800/4324* (2013.01); *A61K 2800/48* (2013.01); *A61K 2800/5426* (2013.01); *A61K 2800/594* (2013.01); *A61K 2800/75* (2013.01); *A61K 2800/884* (2013.01)

(58) Field of Classification Search
CPC .... A61Q 5/10; A61K 2800/884; A61K 8/342; A61K 2800/48; A61K 8/34; A61K 2800/432; A61K 8/447; A61K 2800/5426; A61K 8/92; A61K 2800/594; A61K 2800/4324
USPC .......................................................... 8/405
See application file for complete search history.

(56) References Cited

U.S. PATENT DOCUMENTS

2016/0128915 A1* 5/2016 Konno .................. B65D 83/62
424/62

FOREIGN PATENT DOCUMENTS

| | | |
|---|---|---|
| JP | H11-501947 | 2/1999 |
| JP | 2012-171952 | 9/2012 |
| JP | 2004-285048 | 10/2014 |
| JP | 2017-88502 | 5/2017 |
| WO | WO-2016/166201 | 10/2016 |

OTHER PUBLICATIONS

English translation of the Japanese Patent No. JP2012171952 A (Jan. 27, 2021).*
Search Report and Written Opinion received in International Application No. PCT/JP2018/046659; dated Mar. 7, 2020.

* cited by examiner

*Primary Examiner* — Eisa B Elhilo
(74) *Attorney, Agent, or Firm* — ALG Intellectual Property, LLC

(57) ABSTRACT

A hair coloring method that has a better property of keeping color quality, hardly damages hair, reduces skin damage and is free of paraphenylenediamine when performing hair dye comprises a step of applying a mixture of the following (A) and (B) in a predetermined ratio: (A) a hair coloring agent comprising at least a basic dye, an HC dye, a second amino acid, a first cationic surfactant, a thickener, an oil agent, a first pH adjuster and a wetting agent, wherein the hair coloring agent has a pH of 6.8 or more, and (B) a hair cosmetic comprising at least an alkaline agent, a first amino acid, a higher alcohol having 12 to 22 carbon atoms, a surfactant, and a thickener; a step of providing a predetermined time after applying; and a step of applying a cuticle care agent after the predetermined time.

8 Claims, No Drawings

HAIR COLORING METHOD

TECHNICAL FIELD

The present invention relates to a hair coloring method, and in particular, relates to a hair coloring method using a mixture of a hair cosmetic composition and a hair coloring agent composition capable of hardly damaging hair, reducing skin damage, and having a property of keeping color quality and penetrating dyeing power.

BACKGROUND ART

As hair coloring, there are mainly hair color, which is a permanent hair dye for quasi drugs, and hair manicure and hair color treatment, which are semi-permanent hair dyes for cosmetics. In particular, the hair colors of permanent hair dyes containing paraphenylene diamine (oxidative dye) is mainstream, but in the case of black-based dark colors, since the amount of diamine-based compounds increases. More attention is required.

For example, as a hair coloring composition comprising paraphenylenediamine (oxidative dye), a hair coloring composition characterized by comprising (a) a water-soluble peroxygen bleach; (b) a bleaching aid selected from an organic peroxyacid bleach precursor and/or a preformed organic peroxyacid; and (c) one or more hair coloring agents is known (Patent literature 1).

PRIOR ART LITERATURE

Patent Literature

Patent literature 1: JP-A1-H11-501947

DISCLOSURE OF THE INVENTION

Problems to be Resolved by the Invention

However, in the prior art including the above-mentioned Patent literature 1, those containing paraphenylene diamine (oxidative dye) have a larger amount of diamine based compound in the case of a dark black color as described above. In addition to this, in recent years, skin disorders have been reported due to the use of a substance called paraphenylenediamine (oxidative dye).

In addition, the hair manicure of semi-permanent hair dye is characterized in that the color (acidic dye) penetrates into the inside of hair after a single use and the hair manicure has a feature of a color lasting for 2 to 3 weeks. However, the longer it is left on the scalp, the more difficult it is to remove the dye. Moreover, it is difficult for practitioner to apply to the edge of the hairline. Therefore, such hair dye tends to be avoided in salons and beauty salons because the operator's specific skill is needed and the dyeing is worse than the hair color.

On the other hand, in the above-mentioned hair color, it is possible to dye even cortex (hair cortex. inside hair), but in hair color treatment, since it is aimed that the cuticle (hair skin) and cortex near the hair surface are dyed, in some cases, there was problem that it was not possible to achieve a hair color that has a sufficient property of keeping color quality.

Therefore, the object of the present invention is to provide a hair coloring method that has a better property of keeping color quality, hardly damages hair, reduces skin damage and is free of paraphenylenediamine when performing hair dye.

Means of Solving the Problems

In order to achieve the above object, the present inventors have intensively studied the hair coloring method, and as a result, have found the present invention.

That is, the hair coloring method of the present invention is characterized by comprising a step of applying a mixture of the following (A) and (B) in a predetermined ratio, (A) a hair coloring agent characterized by comprising at least a basic dye, an HC dye, a second amino acid, a first cationic surfactant, a thickener, an oil agent, a first pH adjuster and a wetting agent, wherein the hair coloring agent has a pH of 6.8 or more, (B) a hair cosmetic characterized by comprising at least an alkaline agent, a first amino acid, a higher alcohol having 12 to 22 carbon atoms, a surfactant, and a thickener;

a step of providing a predetermined time after applying; and a step of applying a cuticle care agent after the predetermined time.

Further, in a preferred embodiment of the hair coloring method of the present invention, it is characterized in that the cuticle care agent includes at least one selected from sodium bromate and hydrogen peroxide, a second cationic surfactant, and a second pH adjusting agent.

Further, in a preferred embodiment of the hair coloring method of the present invention, it is characterized in that the method comprises a step of leaving for a certain period of time after application of the cuticle care agent.

Further, in a preferred embodiment of the hair coloring method of the present invention, it is characterized in that the formulation ratio of mixing the hair coloring agent (A) and the hair cosmetic (B) is (A)/(B)=1 to 20.

Further, in a preferred embodiment of the hair coloring method of the present invention, it is characterized in that the alkaline agent is at least one selected from ammonia water, ammonium carbonate, sodium carbonate, ethanolamines, ammonium hydrogen carbonate, and arginine.

Further, in a preferred embodiment of the hair coloring method of the present invention, it is characterized in that the first amino acid or the second amino acid is at least one selected from cysteine, arginine, lysine, or histidine.

Further, in a preferred embodiment of the hair coloring method of the present invention, it is characterized in that at least one of the hair coloring agent, the hair cosmetic and the cuticle care agent contains an antibody production inhibitor.

Further, in a preferred embodiment of the hair coloring method of the present invention, it is characterized in that a hair is warmed in the step of providing a predetermined time after applying.

Effect of Invention

According to the hair color method of the present invention, it has advantageous effects that since it does not contain paraphenylenediamine, in addition to reducing the risk of rash and contact dermatitis, it is difficult to damage the hair even when the use period of the hair color is long. Also, it has advantageous effects that it keeps a good color tone (having a property of keeping color quality) and that it is possible for the practitioner to provide hair coloring to the new part without worrying about adhesion to the scalp.

MODE FOR CARRYING OUT THE INVENTION

The hair coloring method of the present invention is characterized by comprising a step of applying a mixture of the following (A) and (B) in a predetermined ratio,
(A) a hair coloring agent characterized by comprising at least a basic dye, an HC dye, a second amino acid, a first cationic surfactant, a thickener, an oil agent, a first pH adjuster and a wetting agent, wherein the hair coloring agent has a pH of 6.8 or more,
(B) a hair cosmetic characterized by comprising at least an alkaline agent, a first amino acid, a higher alcohol having 12 to 22 carbon atoms, a surfactant, and a thickener;
a step of providing a predetermined time after applying; and
a step of applying a cuticle care agent after the predetermined time. It is preferable that the hair coloring agent contains a basic dye, an HC dye, a second amino acid, a first cationic surfactant, a thickener, an oil agent, a first pH adjuster and a wetting agent, wherein the hair coloring agent has a pH of 6.8 or more, and it is also preferable that the hair cosmetic composition contains an alkaline agent, a first amino acid, a higher alcohol having 12 to 22 carbon atoms, a surfactant, and a surfactant.

First, a hair color agent composition and a hair color agent applicable to the present invention will be described below.

The hair coloring agent composition applicable to the present invention is characterized by comprising a basic dye, an HC dye, an amino acid, a cationic surfactant, a thickener, an oil agent, a pH adjuster and a wetting agent, wherein the hair coloring agent composition has a pH of 6.8 or more. In the hair color composition applicable to the present invention, an adjustment of the pH to 6.8 or more makes it possible to open the cuticle easily, and at the same time, basic amino acids such as L-arginine, L-lysine, L-histidine, and salts thereof can be fed into the hair. As a result, a product capable of being used for coloring while supplementing and repairing basic amino acids that have leaked from the hair in the past (as a hair damage). That is, if the hair coloring agent composition of the present invention is applied, it is possible to open the cuticle, and as a result, it has an advantageous effect that a hair color which has a property of keeping color quality can be achieved.

Further, in a preferred embodiment of the hair coloring agent composition applicable to the present invention, from the viewpoint of easy opening of the cuticle and adjusting pH to 6.8 or more, as the pH adjusting agent mention may be made of at least one selected from citric acid, phosphoric acid, lactic acid, malic acid, ammonia water, ammonium hydrogencarbonate, ammonium carbonate, potassium hydroxide, sodium hydroxide, monoethanolamine, ammonium phosphate, sodium citrate, ammonium citrate, sodium lactate, potassium phosphate, sodium phosphate. From the viewpoint of being weakly alkaline and having little residue on the hair, preferably, as the pH adjuster, mention may be made of ammonium bicarbonate, sodium bicarbonate and the like.

From the viewpoint that the cuticle can be efficiently opened and a property of keeping color quality can be exhibited well, the pH value of the hair coloring agent composition of the present invention can be adjusted to preferably 6.8 or more, more preferably 7.0 to 9.0, still more preferably 7.3 to 8.0.

In addition, in a preferred embodiment of the hair coloring agent composition applicable to the present invention, the amino acid is characterized by being at least one selected from cysteine, arginine, lysine, or histidine. In addition, the amount of the amino acid is not particularly limited, but from the viewpoint of keeping the moisture and flexibility of the hair, it can be set to preferably 0.01 to 0.5% by mass, more preferably 0.01 to 0.3%, still more preferably 0.02 to 0.2 mass %, with respect to the total amount of the composition.

Further, in a preferred embodiment of the hair coloring agent composition applicable to the present invention, the basic dye is characterized by being at least one selected from Basic Blue 3, Basic Blue 7, Basic Blue 99, Basic Red 76, Basic Yellow 57, Basic Brown 16, or Basic Brown 17, in the name of (INCI (INCI: International Nomenclature of Cosmetic Ingredient). Incidentally, INCI (INCI: International Nomenclature of Cosmetic Ingredient) is an international labeling name for cosmetic ingredients prepared by the International Nomenclature Committee (INC). In addition, the amount of the basic dye is not particularly limited, but from the viewpoint that the dyeing power is not strong but damage to the hair is small, it can be preferably 0.0005 to 5% by mass, more preferably 0.01 to 3% by mass, and still more preferably 0.1 to 1% by mass with respect to the total amount of the composition.

Further, in a preferred embodiment of the hair coloring agent composition applicable to the present invention, the HC dye is characterized by being at least one selected from HC Blue 2, HC Yellow 2, HC Yellow 4, HC yellow 5, HC red 1, HC red 3, or HC orange 1, in the name of INCI (INCI: International Nomenclature of Cosmetic Ingredient). Further, the amount of the HC dye is not particularly limited. However, since the HC dye dyes the hair, from the viewpoint of deeper color development, it can be preferably 0.0005 to 5% by mass, more preferably 0.01 to 3% by mass, and still more preferably 0.1 to 1.5% by mass, with respect to the total amount of the composition.

Further, in a preferred embodiment of the hair coloring agent composition applicable to the present invention, from the viewpoint of further improving the touch given to the hair, the cationic surfactant is characterized by being a quaternary ammonium salt and/or a tertiary amine. In addition, in a preferred embodiment of the hair coloring agent composition of the present invention, the quaternary ammonium salt is characterized by being an alkyltrimethylammonium chloride solution, stearyltrimethylammonium chloride, or stearyltrimethylammonium bromide. Further, in a preferred embodiment, the tertiary amine is characterized by being stearic acid dimethylaminopropylamide, stearic acid diethylaminoethylamide, or behenamidopropyldimethylamine. Further, the amount of the cationic surfactant is not particularly limited, but from the viewpoint of improving the hair dyeing ability of the basic dye, it can be preferably 0.01 to 10% by mass, more preferably 0.1 to 5% by mass, and still more preferably 1 to 3% by mass, based on the total amount of the composition.

In addition, the hair color composition applicable to the present invention may contain a thickener, a wetting agent, an oil agent and the like. In the present invention, these thickeners and the like are not particularly limited as long as they do not depart from the effects of the present invention, and a known thicker can be used. As the thickener, from the viewpoint of product stability, for example, mention may be made of hydroxyethyl cellulose, xanthan gum, polyethylene glycol and the like. Further, the amount of the thickener is not particularly limited, but from the viewpoint of improving the stability of the product, it can be preferably 0.05 to 0.8% by mass, more preferably 0.1 to 0.5% by mass with, still more preferably, it can be 0.2 to 0.4 mass %, with respect to the total amount of the composition.

Also, as the wetting agent, mention may be made of glycerin, diglycerin, and 1,3-butylene glycol. Further, the amount of the wetting agent is not particularly limited, but from the viewpoint of easy application of the product, it can be preferably 0.1 to 15% by mass, more preferably 0.5 to 10% by mass, still more preferably 1 to 5% by mass, with respect to the total amount of the composition.

Also, as the oil agent, mention may be made of fats and oils, waxes, hydrocarbons, alkyl glyceryl ethers, esters, silicones, higher alcohols, and the like. Further, the amount of the oil agent is not particularly limited, but from the viewpoint of preventing the drying of the coating leaving time and the stability of the product, it can be preferably 1 to 30% by mass, more preferably 2 to 20% by mass, and still more preferably may be 3 to 15% by mass.

Further, the hair coloring agent applicable to the present invention is characterized by including the hair coloring agent composition applicable to the present invention as described above. The hair coloring agent composition applicable to the present invention can be appropriately included in the hair coloring agent as desired or depending on the use of the hair coloring agent.

In addition, an example of a hair cosmetic composition and a hair cosmetic applicable to the present invention will be described as follows.

The hair cosmetic composition applicable to the present invention is characterized by comprising an alkali agent, an amino acid, higher alcohols having 12 to 22 carbon atoms, a surfactant, and a thickener. The alkaline agent contained in the hair cosmetic composition (basic cuticle swelling agent) can open the cuticle. That is, in hair coloring methods and the like, the cuticle (hair skin) and cortex near the hair surface are dyed, and there are cases where a hair color with sufficiently property of keeping a good color cannot be achieved. However, if the hair cosmetic composition is applied, it is possible to open the cuticle, and as a result, it has an advantageous effect that a hair color which has a property of keeping color quality can be achieved.

In other words, in the past, basic dyes and HC dyes dye cuticles and cortex close to the surface, but by using the hair cosmetic composition (swelling agent), the present inventors have found that it is possible to dye with basic dyes and HC dyes up to deeper parts of the hair.

The pH value of the hair cosmetic composition is not particularly limited, but from the viewpoint that the cuticle can be efficiently opened and the swelling effect can be satisfactorily exhibited, the pH value of the hair cosmetic composition of the present invention can be adjusted to preferably 7.0 to 11.5, more preferably pH 8.5 to 11.5, and still more preferably pH 9.0 to 9.7. The amount of the alkali agent is not particularly limited, but from the viewpoint of efficiently opening the cuticle and exhibiting a good swelling effect, it can be preferably 1 to 3% by mass with respect to the total amount of the composition.

Moreover, the amount of the amino acid is not particularly limited, but from the viewpoint of keeping the moisture and flexibility of the hair, it can be set to preferably 0.01 to 0.5% by mass, more preferably 0.01 to 0.3%, and still more preferably 0.02 to 0.2% by mass, with respect to the total amount of the composition.

In the hair cosmetic composition applicable to the present invention, the higher alcohols having 12 to 22 carbon atoms is not particularly limited, but from the viewpoint of imparting smoothness to the hair, improving the emulsion stability, and adjusting the viscosity, mention may be made of cetyl alcohol, lauryl alcohol, myristyl alcohol, cetostearyl alcohol, stearyl alcohol, and behenyl alcohol and the like.

Further, the amount of the higher alcohols having 12 to 22 carbon atoms is not particularly limited, but from the viewpoint of imparting smoothness to hair, improving emulsification stability and adjusting the viscosity, preferably, the content can be 0.1 to 5.0% by mass, more preferably 0.1 to 3.0% by mass, and still more preferably 0.2 to 2.0% by mass.

In a preferred embodiment, the alkaline agent is not particularly limited, and examples thereof can include at least one selected from ammonia water, ammonium carbonate, sodium carbonate, ethanolamines, ammonium bicarbonate, and arginine. In a preferred embodiment of the hair cosmetic composition applicable to the present invention, the ethanolamine is characterized by being monoethanolamine, diethanolamine, and/or triethanolamine.

Ethanolamines such as monoethanolamine are non-volatile and have little odor, but they remain highly on the hair and may hurt the hair. Further, arginine has a high affinity with hair, but it is weak regarding an action as an alkaline agent and has a mild reaction. Ammonia water has a pungent odor due to its volatility, but it is characterized by little residue on the hair and quick reaction. From this point of view, as the alkaline agent, mention may be made of preferably ammonia water.

Further, in a preferred embodiment, the amino acid may include at least one selected from cysteine, arginine, lysine, and/or histidine.

Although it has been reported that arginine and histidine in the hair decrease with aging, in the present invention, it is possible for arginine, histidine hydrochloride, lysine hydrochloride blended in the hair cosmetic composition (swelling agent) of the present invention to penetrate into the hair and exert a hair repair effect.

The hair cosmetic composition applicable to the present invention may contain a surfactant and a thickener. About these surfactant and a thickener, unless it deviates from the effect of this invention, it does not specifically limit and a well-known one can be used.

Further, in a preferred embodiment, in the hair cosmetic composition (basic cuticle swelling agent) applicable to the present invention, the alkaline agent contained in the hair cosmetic composition can open the cuticle.

In addition, in order to tighten the cuticle etc., after performing hair color using the hair cosmetic composition applicable to the present invention, for example, it is also possible to apply a cuticle care agent including sodium bromate. It is also possible to dye the HC dye, which is easily fading, inside the hair in order to delay the color fading.

Further, a hair cosmetic applicable to the present invention is characterized by including the above-described hair cosmetic composition applicable to the present invention.

The above is an explanation of examples of hair cosmetics and hair coloring agents.

In the present invention, a mixture of these hair color agents and hair cosmetics in a predetermined ratio can be applied. The reason why both of the hair color agents and hair cosmetics are mixed is that the present inventors have found that, when they are used as a mixture, they are deeply dyed and have good color retention, as compared with the case where they are used alone. It suffices to mix both, and the predetermined ratio is not particularly limited, but in a preferred embodiment, it is characterized in that the compounding ratio for mixing the (A) hair coloring agent and the (B) hair cosmetic is (A)/(B)=1 to 20. That is, from the viewpoint of hair dyeing power, the blending ratio of the hair coloring agent and the hair cosmetic can be preferably 1 to 20:1 by mass ratio, more preferably 5 to 15:1 by mass ratio, and further preferably 8 to 12:1 by mass ration.

Further, in the present invention, from the viewpoint that the cuticle can be efficiently opened, the swelling effect can be satisfactorily exhibited, and the dyeing can be advanced, a predetermined time can be provided after the application. Further, in a preferred embodiment of the hair coloring method of the present invention, in the step of providing a predetermined time after the application, the hair is warmed from the viewpoint of enhancing the permeation dyeing power. The warming time is also not particularly limited if desired, but from the viewpoint of efficiently dyeing hair, it can be 1 to 60 minutes, preferably 5 to 40 minutes. From the viewpoint of the treatment process time, the temperature may be raised to about 40° C. in about 10 minutes to (about 10 minutes or more) and kept at the temperature for about 20 minutes. Further, in a preferred embodiment of the hair coloring method of the present invention, the application portion may be covered with a wrap and warmed using a hair dryer during the time for leaving the hair with application.

Further, the present invention may include a step of applying a cuticle care agent after the predetermined time. In addition, in a preferred embodiment of the hair coloring method of the present invention, the present invention may include a step of leaving for a certain time, from the viewpoint that the cuticle (hair scalp) that has been opened is tightened and dyeing the HC dye inside the hair, after the cuticle care agent is applied. Although the standing time is not particularly limited, for example, the standing time can be 1 to 20 minutes, preferably 1 to 10 minutes.

In addition, in a preferred embodiment of the hair coloring method of the present invention, after the hair cosmetic composition and the hair coloring agent are mixed and applied, a step of applying a cuticle care agent containing at least one selected from sodium bromate and hydrogen peroxide, a second cationic surfactant and a second pH adjusting agent may be included. Moreover, as the second pH adjuster, an acidic pH adjuster can be blended. Further, from the viewpoint of returning to a healthy hair condition (isoelectric band pH 4.5 to 5.5), as the pH adjusting agent, mention may be made of organic acids such as citric acid, phosphoric acid, phytic acid, lactic acid, malic acid, and acidic amino acids such as glutamic acid and the like.

Further, in a preferred embodiment of the hair coloring method of the present invention, the amino acid is characterized by being at least one selected from cysteine, arginine, lysine, or histidine. As to the amino acid, reference may be made to the above descriptions in the hair cosmetics etc., applicable to the present invention as mentioned above.

Further, in a preferred embodiment of the hair coloring method of the present invention, the first or second amino acid is characterized by being at least one selected from cysteine, arginine, lysine, or histidine. As to the first or second amino acid, reference may be made to the above descriptions in the hair cosmetics and hair coloring agent etc., applicable to the present invention as mentioned above.

Further, in a preferred embodiment of the hair coloring method of the present invention, the hair coloring method may further include a step of applying a shampoo agent. When applying a shampoo agent to hair, from a viewpoint of removing obstruction factors, such as hairdressing agents and sebum, it may be applied before the treatment of hair cosmetics. In this case, as the shampoo agent, preferably, estrone shampoo, estrone black, applecel shampoo premium, nanosupple cleansing shampoo and the like (manufacturer and distributor of these products: Sunny Place Co., Ltd.) can be used.

The shampoo agent may also be applied after coloring. In this case, the pH of the shampoo agent is preferably weakly acidic. Further, as the shampoo agent, estrone shampoo or applecel shampoo premium (shampoo agent, manufacturer and distributor: Sunny Place Co., Ltd.) can be preferably used.

Further, in a preferred embodiment of the hair coloring method of the present invention, at least one of the hair coloring agent, the hair cosmetic, and the cuticle care agent may further contain an antibody production inhibitor. As the antibody production inhibitor, from the viewpoint of prevention and improvement of allergic diseases, mention may be made of pomegranate seed extract, mushrooms extract belonging to the genus *agaricus*, etc., willow mint extract, edelweiss extract and the like.

For example, the case where a pomegranate seed extract is used as an antibody production inhibitor will be described below as an example. Pomegranate seed extract is an extract derived from pomegranate seeds. The pomegranate seed extract applied to the present invention covers all pomegranate seed extracts as long as they are derived from pomegranate seeds.

Further, in a preferred embodiment, the pomegranate seed extract is characterized by containing punicic acid or ellagic acid. The pomegranate seed extract can be obtained, for example, by the following method. It is characterized in that at first, the crushed product obtained by crushing pomegranate seeds is immersed in at least one solvent selected from the group consisting of ethanol, methanol, water and hexane, the supernatant is separated to obtain the pomegranate seed extract. For example, it can be shaken and extracted. In shaking extraction, for example, extraction can be performed by setting the rotator in a low temperature room such as about 4° C. and rotating.

More specifically, first, pomegranate seeds are prepared. Pomegranate seeds are washed if necessary and dried. It is preferable to perform the drying sufficiently. This is because the subsequent pulverization is performed uniformly.

Next, the pomegranate seeds are crushed. The pulverization method is not particularly limited, and a known pulverizer such as a ball mill, a hammer mill, a roller mill, a rod mill, a sample mill, a stamp mill, a disintegrator, a mortar, and a blender with a cooling device can be used. Moreover, since it is considered that the pomegranate seed composition is decomposed due to the heat generated during the pulverization, the pulverization time can be set to several seconds and it can be repeated about a dozen of times.

Next, the pomegranate seeds are crushed to obtain a crushed product, and then the crushed product is immersed in various solvents. The solvent in this case is not particularly limited, and the solvent can be appropriately set according to the desired effect. Further, in a preferred embodiment of the method for producing a pomegranate seed extract of the present invention, the solvent is characterized in that the solvent is at least one selected from the group consisting of ethanol, methanol, hexane and water. The solvent may be a polar or nonpolar solvent such as ethanol, methanol, water, hexane, ethyl acetate, chloroform or acetone. Preferably, methanol, ethanol and water, etc. can be mentioned.

Immersion can be performed under gentle stirring. The pulverized product is dipped in various solvents to obtain various solutions. Various solutions may be stirred depending on the state of the solution, and the solution may be left as it is depending on the case. The stirring is not particularly limited, but the stirring can be continued for 10 hours to 48 hours, preferably about 1 day (24 hours).

Then, the pomegranate seed extract can be obtained by separating the supernatant. If necessary, the supernatant is evaporated to dryness. Evaporation to dryness can be carried out using an evaporator on a warm bath at 20° C. to 60° C., preferably 37° C. to 40° C. By evaporating to dryness, the pomegranate seed extract can be stored for a long period of time.

The components contained in pomegranate seeds are sorted according to their physical properties by extracting pomegranate seeds with solvents having different polarities. Therefore, the type and content of the components of the pomegranate seed extract differ depending on the solvent used.

Moreover, an example of the hair coloring method of the present invention will be described below.

1) An appropriate pre-shampoo is performed to remove hair styling agents and stains.
2) A mixture of a hair color agent (containing a hair dye component) and a hair cosmetic (containing a basic cuticle swelling agent) applicable to the present invention in a predetermined ratio is applied to the hair by a brush.
3) The applied hair is covered with a plastic wrap to heat it with a hair dryer, and to leave it for about 30 minutes.
4) In this approximately 30 minutes, the temperature is maintained at approximately 40° C. in approximately 10 minutes by a hair dryer, and then the temperature is maintained for approximately 20 minutes.
5) After 4), the cuticle care agent is applied to the hair thoroughly and leave it for about 6 minutes.
6) After 5), a hair is washed with water at appropriate temperature and shampoo agent.
7) After towel drying, the hair is dried with a hair dryer.

EXAMPLE

As mentioned below, an embodiment of a hair coloring agent, a hair cosmetic and a cuticle care agent applicable to the present invention will be concretely explained in more detail with reference to Examples, but the invention is not intended to be interpreted as being limited to the following Examples.

First, a hair coloring agent applicable to the present invention was prepared.

Regarding the alkaline agent (pH adjusting agent), from the viewpoint that it is weakly alkaline and skin irritation does not easily occur, in the example, a test was conducted using ammonium hydrogen carbonate as an example.

In addition, about 80% of human hair is composed of keratin proteins derived from amino acid, L-cysteine is an amino acid that is also abundant in the hair. Therefore, L-cysteine and its salts were tried for the purpose of keeping the hair moisturized and flexible. Typical basic amino acids include L-arginine, L-lysine and L-histidine, but these are known to flow out when damaged, and there was found that 0.01 to 0.5% by mass of basic amino acids and salts thereof are preferable.

Table 1 shows the components of an example of the hair coloring agent composition in one embodiment of the present invention.

TABLE 1

|  | Abbreviation or Product name | Components(Display name) | Manufacturer | Compounding amount (% by mass) |
|---|---|---|---|---|
|  | Water | Water |  | Residue |
| Water phase | Concentrated glycerin for cosmetic | Glycerin | Sakamoto Pharmaceutical Co., Ltd. | 1.00 |
|  | 1,3-butylene glycol-P | BG | KH Neochem Co., Ltd. | 1.00 |
|  |  | Pentylene glycol |  | 1.00 |
|  |  | Hydroxyethyl cellulose |  | 0.25 |
|  | Catinal STB-70 | Steartrimonium bromide | Toho Chemical Industry Co., Ltd. | 1.50 |
|  |  | Isopropanol |  | 1.00 |
| Oil phase | KALCOL 4098 | Myristyl alcohol | Kao Corporation | 5.00 |
|  | Lanette 22 | Behenyl alcohol | BASF Japan Co., Ltd. | 1.00 |
|  | Cegesoft C24 | Ethylhexyl palmitate | BASF Japan Co., Ltd, | 2.00 |
|  | Cutina CP | Cetyl palmitate | BASF Japan Co., Ltd. | 1.00 |
|  |  | Glycol stearate |  | 2.00 |
|  | Refined shea butter | Shea fat | Koei Kogyo Co., Ltd. | 1.00 |
| Alkaline agent |  | Ammonium hydrogen carbonate |  | 1.00 |
| Preservatives and refreshing ingredients | Hisolve EPH | Phenoxyethanol | Toho Chemical Industry Co., Ltd. | 0.60 |
|  | L-Menthol | Menthol | K. Kobayashi & Co., Ltd. | 0.10 |
|  | Dehydrated ethanol | Ethanol | Kenei Pharmaceutical Co., Ltd. | 1.00 |
| Antiinflammatory component | Dipotassium glycyrrhizinate | Glycyrrhizic acid 2K | Maruzen Pharmaceutical Co., Ltd. | 0.10 |
| Antiallergic component | Pomegranate seed extract BG-100 | Pomegranate seed extract | KOEI KOGYO Co., Ltd | 0.10 |
| Pigment |  | Basic blue 99 |  | 0.30 |
|  |  | Basic brown 16 |  | 0.50 |

TABLE 1-continued

| Abbreviation or Product name Water | Components(Display name) Water | Manufacturer | Compounding amount (% by mass) Residue |
|---|---|---|---|
| | HC blue 2 | | 0.60 |
| | HC yellow 4 | | 0.20 |
| | HC yellow 2 | | 0.10 |
| Amino acid group L-Arginine | Arginine | Kyowa Hakko Bio Co., Ltd. | 0.10 |
| L-histidine hydrochloride monohydrate | Histidine HCl | Wako Pure Chemical Industries, Ltd. | 0.02 |
| L-lysine hydrochloride | Lysine HCl | Wako Pure Chemical Industries, Ltd. | 0.02 |
| | Total(% by mass) | | 100.00 |
| | pH | | 8.00 |

The preparation method is as follows.

Preparation Method:

1. The aqueous phase (water phase) of Table 1 is warmed to 75-77° C. with stirring.
2. The oil phase in Table 1 is stirred while heating to 77-79° C. to make it uniform.
3. The pigment is added to water phase heated to 75-77° C. to homogenize, the oil phase is add to the mixture to emulsify and stir until uniform.
4. The content is slowly cooled, and when the temperature of the content is 43° C. or lower, the preservative, the refreshing component, the antiinflamator component, and the amino acid group are added and stirred until uniform, and then cooled to 32° C. or lower.

Moreover, the following models and electrodes were used for pH measurement.

Model of pH meter: F-71 (Horiba, Ltd.)

pH meter electrode: Type 9615 (Horiba, Ltd.)

In addition, a hair colorant applicable to the present invention was actually prepared, and a color fading test was performed on the hair bundle. As a result, it was found that the hair coloring agent applicable to the present invention was extremely excellent in color fading.

Conventionally, when a hair coloring agent that does not contain paraphenylenediamine is applied and left as it is, although, the base color is a basic dye and HC dye, which are considered to be safer than oxidative dyes, since it was dyed on the hair, the color persistence after the hair dyeing was bad, and there was the fault that it was easy to lose color due to repeated shampooing. It was found that In contrast to conventional hair coloring agents, the hair coloring agent applied to the present invention not only the base color easily penetrates but also it can be applied from the new part to the hair tip without worrying about adhesion to the scalp because it does not contain an acidic dye.

Thus, in the hair coloring agent etc., applicable to the present invention, when performing hair dye, compared with conventional hair color and hair manicure, in the conventional method, there are problems that 1) if the hair is damaged by repeated dyeing, the hair strength is reduced and elasticity is lost to thin a hair (In the case of hair color of prior art), 2) if the scalp rash occurs, the rash part will stain and be difficult to remove (in the case of hair manicure of prior art). However, in the present invention, there is no problem of the above, it was found that hair cosmetics with good penetration and dyeing power can be provided. In other words, in the present invention, it has also been found that safety is provided in addition to color retention.

Next, a hair cosmetic applicable to the present invention was prepared.

Regarding alkaline agents, ammonia water, ammonium carbonate, sodium carbonate, triethanolamines such as mono, di, or triethanolamines, ammonium hydrogen carbonate, arginine, and the like are considered. However, ethanolamines such as monoethanolamine are non-volatile and have little odor, but they remain highly on the hair and may hurt the hair. In addition, arginine has a high affinity with hair, but it is weak as to an action as an alkaline agent and has a mild reaction. Aqueous ammonia is the irritating odor due to volatile, but has a property that it has little residue on the hair and reacts quickly.

In addition, about 80% of human hair is composed of keratin proteins derived from amino acid, L-cysteine is an amino acid that is also abundant in the hair. Therefore, L-cysteine and its salts were tried for the purpose of keeping the hair moisturized and flexible. Typical basic amino acids include L-arginine, L-lysine and L-histidine, but these are known to flow out when damaged, and there was found that 0.01 to 0.5% by mass of basic amino acids and salts thereof are preferable.

Table 2 shows the components of an example of the hair cosmetic composition in one embodiment of the present invention.

TABLE 2

|  | Abbreviation or Product name | Components | Manufacturer |
| --- | --- | --- | --- |
|  | Purified water |  |  |
| Alkaline agent | Reagent grade 25% Ammonia water | 25% Ammonia water | Osaka Sasaki Chemical Co., Ltd. |
| Amino acid group | CSKE-200 | L-Cysteine hydrochloride | Osaka Sasaki Chemical Co., Ltd. |
|  | L-Arginine | L-Arginine | Wako Pure Chemical Industries, Ltd. |
|  | L-Histidine | L-Histidine | Wako Pure Chemical Industries, Ltd. |
| Antiallergic component | Pomegranate seed extract BG-100 | Pomegranate seed extract | KOEI KOGYO Co., Ltd |
| Common ingredients | Concentrated glycerin for cosmetic | Concentrated glycerin | Sakamoto Pharmaceutical Co., Ltd. |
|  | SILK-1000 | Hydrolyzed silk | Seiwa Kasei Co., Ltd. |
|  | Kohtamin 60W | Cetyltrimethylammonium chloride | Kao Corporation |
|  | — | Fragrance | Kotobuki Fragrance Co., Ltd. |
| Emulsifying stability and viscosity-imparting | EMACOL VS | Cetyl alcohol Lauryl alcohol Polyoxyethylene oleyl ether Polyoxyethylene lauryl ether Sodium lauryl sulfate | Sanei Chemical Co., Ltd. |

Table 3 shows an adjustment example relating to the component example of the hair cosmetic according to the embodiment of the present invention.

TABLE 3

|  |  | Components(Display name) | Compounding amount |
| --- | --- | --- | --- |
| A phase | Base | Water | Residue |
|  | Alkaline agent | Ammonia water | 2.40 |
|  | Amino acid group | Cysteine HCl | 1.00 |
|  |  | Arginine | 1.00 |
|  |  | Histidine | 1.00 |
| B phase | Antiallergic component | Pomegranate seed extract | 0.0025 |
|  | Common ingredients | Glycerin | 1.00 |
|  |  | Hydrolyzed silk | 0.50 |
|  |  | Cetyltrimethylammonium chloride | 1.50 |
|  |  | Fragrance | 0.20 |
| C phase | Emulsifying stability and viscosity-imparting ingredients | Cetyl alcohol | 1.92 |
|  |  | Lauryl alcohol | 0.24 |
|  |  | Polyoxyethylene oleyl ether | 0.39 |
|  |  | Polyoxyethylene lauryl ether | 0.27 |
|  |  | Sodium lauryl sulfate | 0.18 |
|  |  | Total (% by mass) | 100.00 |
|  |  | pH | 10.38 |

The preparation method is as follows.
Preparation Method:
1. After confirming the dissolution of the amino acid group in the purified water of Phase A in Table 3, the alkaline agent is mixed uniformly.
2. Next, while stirring the A phase of Table 3, the B phase of Table 3 is added and mixed uniformly.
3. Add Phase C in Table 3 with moderate stirring and stir until uniform.

Moreover, the following models and electrodes were used for pH measurement.
Model of pH meter: F-71 (Horiba, Ltd.)
pH meter electrode: Type 9615 (Horiba, Ltd.)

Table 4 shows an example of ingredients of the cuticle care agent in one embodiment of the present invention. The cuticle care agent includes an action of improving the condition of the cuticle such as adjusting and tightening the cuticle. In other words, it is not limited to the action of adjusting and tightening.

TABLE 4

| Abbreviation or Product name | Components | Manufacturer |
| --- | --- | --- |
| Sodium bromate | Sodium bromate | KANTO CHEMICAL CO., INC. |
| Chitofilmer | Hydroxypropyl Chitosan solution | ICHIMARU PHARCOS Co., Ltd. |
| Pomegranate seed extrac BG-100 | Pomegranate seed extrac | KOEI KOGYO Co., Ltd. |
| Citric acid | Citric acid | Showa Kako Corporation |
| L-Histidine monohydrochloride monohydrate | L-Histidine monohydrochloride | Wako Pure Chemical Industries, Ltd. |
| L-Arginine hydrochloride | L-Arginine hydrochloride | KYOWA HAKKO BIO CO., LTD. |
| Kohtamin 24P | Lauryl trimethyl ammonium chloride solution | Kao Corporation |
| Genagen CAB818J | Coconut, oil fatty acid amide propyl betaine liquid | Clariant Japan K.K. |

Table 5 shows an example of an adjustment method relating to the cuticle care agent applicable to the present invention according to the embodiment of the present invention.

TABLE 5

| | | Components(Display name) | Compounding amount |
| --- | --- | --- | --- |
| A phase | | Water | Residue |
| | Oxidant | Sodium bromate | 10.00 |
| | Chitosan derivative | Hydroxypropyl chitosan | 0.10 |
| | Antiallergic component | Pomegranate seed extract | 0.0025 |
| | Basic amino acid | Histidine HCl | 0.05 |
| | derivative | Arginine HCl | 0.05 |
| | pH adjuster | Citric acid | q.s. |
| B phase | Cationic surfactant | Lauryl trimethyl ammonium chloride solution | 0.27 |
| C phase | Amphoteric surfactant | Cocamidopropyl betaine | 1.50 |
| | | Total (% by mass) | 100.00 |
| | | pH | 6.67 |

The preparation method of the cuticle care agent applicable to the present invention is as follows.
Preparation Method:
1. The residue components of Phase A in Table 5 in the purified water are mixed uniformly
2. Next, while stirring the A phase of Table 5, the B phase of Table 5 is added and mixed uniformly.
3. Add Phase C in Table 5 with moderate stirring and stir until uniform.
4. The pH of the preparation is adjusted to about pH 5.4 with citric acid in order to adjust the isoelectric band of hair (pH 4.5 to 5.5).

Moreover, the following models and electrodes were used for pH measurement.
Model of pH meter: F-71 (Horiba, Ltd.)
pH meter electrode: Type 9615 (Horiba, Ltd.)

Moreover, as a result of the patch test of the above hair cosmetics and hair coloring agents, the skin irritation index was 0.0 to 2.5 for 20 subjects, and it was confirmed that they were all safe products.

Next, using hair coloring agents (one kind used in the present invention and other companies' products), hair cosmetics and cuticle care agents, hair coloring is performed, and the comparison results regarding tensile breaking strength, change in lightness due to washing, and water content of hair dyeing will be described.

Example 1

Commercially available black hair 100% untreated hair (product number: BS-B-A, manufactured by Burex Co.) weight 1 g, length 10 cm is used as a hair sample, and a mixture of a hair color agent (trade name: kiragami Painter A (a hair painter A), manufactured by Sunny Place Co. Ltd.) and a base cuticle swelling agent (trade name: kiragami Painter B (a hair painter B), manufactured by Sunny Place Co., Ltd.) in a blending ratio (A:B=10:1) was applied uniformly with a brush, and then covered with wrap, and warm for about 30 minutes using a dryer (heat up to about 40° C., in about 10 minutes and keep the temperature for about 20 minutes). Then, a cuticle care agent (trade name: kiragami Painter C (a hair painter C), manufactured by Sunny Place Co., Ltd.) was applied to the whole by rubbing and left for about 6 minutes. Then, it was rinsed with hot water having a proper temperature and a shampoo containing a pomegranate seed extract (trade name: Estrone shampoo, manufactured by Sunny Place Co., Ltd.), and dried with a hair dryer to finish. This process from hair dyeing to washing and drying was repeated 5 times to create dyed hair. Moreover the compounding ratio is the ratio of the mass of the product.

Comparative Example 1

An oxidative hair dye (trade name: Igora Royal Pixam-G G-B6, manufactured by Henkel Japan) and a developer having 6% hydrogen peroxide at a 1:1 ratio were mixed, and an obtained mixture was applied to the same hair sample as in Example 1. After coating, it was left at room temperature for 30 minutes. Thereafter, the hair was washed with hot water at an appropriate temperature in the same manner as in Example 1, and dried with a hair dryer to finish. This process from hair dyeing to washing and drying was repeated 5 times to create dyed hair.

Comparative Example 2

An oxidative hair dye (trade name: Promaster B-6/5, manufactured by Hoyu Co., Ltd.) and a developer having 6% hydrogen peroxide at a 1:1 ratio were mixed, and an obtained mixture was applied to the same hair sample as in Example 1 (and Comparative Example 1). After coating, it was left at room temperature for 30 minutes. Thereafter, the hair was washed in the same manner as in Example 1, and dried with a hair dryer to finish. This process from hair dyeing to washing and drying was repeated 5 times to create dyed hair.

For Example 1, Comparative Example 1 and Comparative Example 2, using a high-sensitivity hair tension tester (type: KES-G1-SH, manufactured by Kato Tech Co., Ltd.), the tensile cutting strength per hair was measured at the tensile speed of 1.2 cm/minutes.

Table 6 shows the results of tensile cutting strength of Example 1, Comparative Example 1 and Comparative Example 2. The tensile cutting strength of Example 1 (average 4.1 (gf/P)) was 1.07 times comparing with that of Comparative Example 1 (average 3.81 (gf/P)), and was 1.13 times comparing with that of Comparative Example 2 (3.61 (gf/P))·P)).

TABLE 6

|  |  | Example1 | Comparative Example 1 | Comparative Example 2 |
|---|---|---|---|---|
| Load value of breaking strength point (gf/P) | 1 | 3.94 | 5.21 | 2.88 |
|  | 2 | 3.06 | 3.80 | 4.32 |
|  | 3 | 4.67 | 5.14 | 4.56 |
|  | 4 | 3.81 | 4.43 | 3.89 |
|  | 5 | 5.34 | 4.14 | 2.35 |
|  | 6 | 4.67 | 4.64 | 5.39 |
|  | 7 | 3.93 | 2.87 | 4.35 |
|  | 8 | 3.03 | 4.06 | 5.29 |
|  | 9 | 3.64 | 5.09 | 1.96 |
|  | 10 | 5.05 | 4.08 | 5.03 |
|  | 11 | 3.61 | 4.82 | 3.06 |
|  | 12 | 4.40 | 3.45 | 3.25 |

TABLE 6-continued

|  | Example1 | Comparative Example 1 | Comparative Example 2 |
|---|---|---|---|
| 13 | 4.44 | 3.91 | 3.50 |
| 14 | 4.35 | 4.41 | 4.38 |
| 15 | 4.22 | 2.40 | 4.19 |
| 16 | 4.45 | 4.34 | 3.59 |
| 17 | 2.11 | 4.37 | 3.24 |
| 18 | 4.17 | 4.03 | 3.14 |
| 19 | 2.93 | 4.41 | 2.96 |
| 20 | 3.80 | 3.09 | 3.40 |
| 21 | 3.45 | 3.83 | 2.64 |
| 22 | 4.96 | 4.40 | 5.12 |
| 23 | 2.15 | 2.82 | 4.04 |
| 24 | 4.84 | 4.51 | 4.36 |
| 25 | 3.78 | 4.69 | 3.76 |
| 26 | 4.34 | 1.47 | 2.69 |
| 27 | 4.07 | 4.05 | 3.98 |
| 28 | 3.52 | 2.83 | 3.40 |
| 29 | 4.13 | 4.22 | 2.46 |
| 30 | 5.10 | 3.65 | 3.74 |
| 31 | 4.02 | 3.01 | 3.17 |
| 32 | 3.14 | 2.20 | 2.11 |
| 33 | 4.38 | 3.97 | 4.30 |
| 34 | 4.89 | 3.19 | 2.54 |
| 35 | 4.18 | 4.40 | 4.00 |
| 36 | 3.48 | 3.09 | 4.04 |
| 37 | 5.45 | 1.69 | 3.65 |
| 38 | 4.01 | 3.15 | 5.27 |
| 39 | 4.90 | 5.37 | 1.61 |
| 40 | 4.62 | 3.25 | 2.94 |
| Total of from 1 to 40 | 163.03 | 152.48 | 144.55 |
| Average | 4.08 | 3.81 | 3.61 |

Reference Example 1 (Creation of Damaged Hair)

Next, we created damaged hair for comparison of tensile cutting strength and moisture measurement described below. A bleaching agent (trade name: bleaching powder, manufactured by Number Three) and a developer of 6% hydrogen peroxide at a ratio of 1:3 were mixed, and an obtained mixture was applied to the same hair sample as in Example 1. After coating, it was left at room temperature for 30 minutes to perform a bleaching treatment.

Reference Example 2

A hair coloring agent (trade name: kiragami Painter A, manufactured by Sunny Place Co., Ltd.) was evenly applied to the created damaged hair with a brush, and then the hair was covered with wrap and heated for 30 minutes using a hair dryer (The temperature is raised to around 40° C. within 10 minutes and kept for 20 minutes). Then, the hair was washed in the same manner as in Example 1 and dried with a hair dryer to finish, and dyed hair was prepared.

Example 2

In the same manner as in Example 1, a hair coloring agent (trade name: kiragami Painter A, manufactured by Sunny Place Co., Ltd.) and a hair cosmetic (sales name: kiragami Painter B, manufactured by Sunny Place Co., Ltd.) were mixed so that A was 10 and B was 1 in a ratio to obtain a mixture, and the mixture was evenly applied to the created damaged hair with a brush. And then the hair covered with wrap and heated for 30 minutes using a hair dryer (the temperature is raised to around 40° C. in 10 minutes, and keep the temperature for 20 minutes). After that, a cuticle care agent (trade name: kiragami Painter C, manufactured by Sunny Place Co., Ltd.) was applied to the entire surface by rubbing and left for 6 minutes. Then, the hair was washed in the same manner as in Example 1 and dried with a hair dryer to finish, and dyed hair was prepared.

With respect to Reference Example 1, Reference Example 2 and Example 2, the same machine as in Example 1 was used to measure the tensile cutting strength per hair at a tensile speed of 1.2 cm/min. Table 7 shows the measurement results. The breaking strength of Reference Example 1 (no coloring of damaged hair) was 3.18 (gf/P), whereas the breaking strength of Reference Example 2 (only the coloring agent was applied to damaged hair) was 3.62 (gf/P). (1.13 times). The breaking strength of Example 2 (the same treatment as in Example 1 for damaged hair) was 3.91 (gf/P) (1.23 times) comparing with that of the damaged hair. The reference example 2 is used as a hair color treatment generally used at home, and it is possible to use this method or the bright hair painter A alone, but as shown in the Example 2, it was found that the tensile strength of hair increased when the three products A, B and C were used.

TABLE 7

|  |  | Reference Example1 | Reference Example2 | Example2 |
|---|---|---|---|---|
| Load value of breaking strength point (gf/P) | 1 | 2.96 | 3.83 | 3.60 |
|  | 2 | 3.08 | 2.29 | 4.04 |
|  | 3 | 3.18 | 2.99 | 4.36 |
|  | 4 | 2.57 | 3.47 | 3.59 |
|  | 5 | 2.80 | 3.42 | 3.80 |
|  | 6 | 4.60 | 4.98 | 3.84 |
|  | 7 | 3.79 | 3.10 | 3.20 |
|  | 8 | 2.79 | 3.48 | 4.66 |
|  | 9 | 2.90 | 4.01 | 4.91 |
|  | 10 | 2.21 | 3.55 | 3.84 |
|  | 11 | 4.14 | 4.71 | 3.15 |
|  | Total of from 1 to 11 | 35.02 | 39.83 | 42.99 |
|  | Average | 3.18 | 3.62 | 3.91 |

Next, the dyeing conditions of the coloring using only the coloring agent for the same hair sample and the coloring applying the hair cosmetic and the cuticle care agent were measured for the lightness for each number of times of hair washing, and the results were compared.

Reference Example 3

Commercially available 30% human white hair mixture with a weight of 1 g and a length of 10 cm (product number: BM-MIX-A, manufactured by Vyrax) was used as a hair sample, and a hair color agent (brand name: kiragami Painter A, manufactured by Sunny Place Co. Ltd.) is evenly applied to the hair sample with a brush, and then the hair covered with a wrap and heated for 30 minutes using a hair dryer (the temperature is raised to around 40° C. in 10 minutes, and the temperature is kept for 20 minutes). Then, the hair was washed in the same manner as in Example 1 and dried with a hair dryer to finish, and dyed hair was prepared. The lightness (L *) was measured by using a spectrophotometer (model: CM-2600d, manufactured by Konica Minolta Co., Ltd.) for the difference in color depending on the number of times the hair was washed.

Reference Example 4

Commercially available 30% human white hair mixture with a weight of 1 g and a length of 10 cm was used as a hair sample (product number: BM-MIX-A, manufactured by Vurex). A basic cuticle swelling agent (brand name: kiragami Painter B, manufactured by Sunny Place Co. Ltd.) is left with a brush for about 5 to 8 minutes, then washed with water and dried with a hair dryer. After that, a hair color agent (trade name: kiragami Painter A, manufactured by Sunny Place) was uniformly applied with a brush, and then covered with a wrap, heated for 5 minutes using a hair dryer, and then left for about 15 minutes. After that, a cuticle care agent (trade name: kiragami Painter C, manufactured by Sunny Place Co., Ltd.) was applied to the whole by rubbing and left for about 5 minutes. Then, the hair was washed in the same manner as in Example 1 and dried with a hair dryer to finish, and dyed hair was prepared. The difference in color depending on the number of times the hair was washed was measured for lightness (L *) according to the same manner as in Comparative Example 5.

Example 3

Commercially available 30% human white hair mixture with a weight of 1 g and a length of 10 cm (product number: BM-MIX-A, made by Vyrax) was used as a hair sample, and a hair color agent (brand name: kiragami Painter A, manufactured by Sunny Place Co. Ltd.) and a hair cosmetics (trade name: kiragami Painter B, manufactured by Sunny Place Co., Ltd.) are mixed in a mixing ratio of A:B=10:1, which are evenly applied to the hair sample with a brush and covered with a wrap. And then the hair sample was heated for 30 minutes (heat up to around 40° C. in 10 minutes and keep temperature for 20 minutes). Then, a cuticle care agent (trade name: kiragami Painter C, manufactured by Sunny Place Co., Ltd.) was applied to the whole by rubbing and left for about 6 minutes. Then, the hair was washed in the same manner as in Example 1 and dried with a hair dryer to finish, and dyed hair was created. The difference in color depending on the number of times the hair was washed was measured for lightness (L *) in the same manner as in Comparative Examples 4 and 5. Moreover, the closer L* is to 0, the darker it is.

Table 8 shows the lightness measurement results for each number of times of washing with respect to Reference Example 3, Reference Example 4 and Example 3. From before shampooing (that is, immediately after hair dyeing treatment) to after shampooing 35 times, the lightness of Reference Example 3 (hair dyeing with a hair coloring agent alone) decreased by 0.1, and the lightness of Reference Example 4 decreased by 1.43. In Example 3, the brightness was reduced to 0.09. That is, Example 3 showed less discoloration due to washing hair than the other two cases.

TABLE 8

|  | L* | ΔL |
|---|---|---|
| Reference Example 3 |  |  |
| Dyed hair using only hair coloring agent Before washing | 20.48 |  |
| Dyed hair using only hair coloring agent 5 times of washing hair | 19.51 | −0.96 |

TABLE 8-continued

| | L* | ΔL |
|---|---|---|
| Dyed hair using only hair coloring agent 10 times of washing hair | 20.47 | −0.01 |
| Dyed hair using only hair coloring agent 15 times of washing hair | 18.49 | −1.98 |
| Dyed hair using only hair coloring agent 20 times of washing hair | 21.58 | 1.10 |
| Dyed hair using only hair coloring agent 25 times of washing hair | 22.75 | 2.27 |
| Dyed hair using only hair coloring agent 30 times of washing hair | 21.70 | 1.22 |
| Dyed hair using only hair coloring agent 35 times of washing hair | 20.34 | −0.14 |
| Reference Example 4 | | |
| Dye hair applied in the order of painter B, A, C Before washing | 13.87 | |
| Dye hair applied in the order of painter B, A, C 5 times of washing hair | 12.21 | −1.66 |
| Dye hair applied in the order of painter B, A, C 10 times of washing hair | 13.36 | −0.51 |
| Dye hair applied in the order of painter B, A, C 15 times of washing hair | 11.27 | −2.60 |
| Dye hair applied in the order of painter B, A, C 20 times of washing hair | 12.70 | −1.17 |
| Dye hair applied in the order of painter B, A, C 25 times of washing hair | 13.50 | −0.37 |
| Dye hair applied in the order of painter B, A, C 30 times of washing hair | 14.97 | 1.10 |
| Dye hair applied in the order of painter B, A, C 35 times of washing hair | 15.30 | 1.43 |
| Example 3 | | |
| Dyed hair applying painter (mixture of A and B) and then applying C Before washing | 13.11 | |
| Dyed hair applying painter (mixture of A and B) and then applying C 5 times of washing hair | 11.67 | −1.44 |
| Dyed hair applying painter (mixture of A and B) and then applying C 10 times of washing hair | 11.43 | −1.68 |
| Dyed hair applying painter (mixture of A and B) and then applying C 15 times of washing hair | 12.51 | −0.60 |
| Dyed hair applying painter (mixture of A and B) and then applying C 20 times of washing hair | 12.80 | −0.31 |
| Dyed hair applying painter (mixture of A and B) and then applying C 25 times of washing hair | 11.93 | −1.18 |
| Dyed hair applying painter (mixture of A and B) and then applying C 30 times of washing hair | 12.95 | −0.16 |
| Dyed hair applying painter (mixture of A and B) and then applying C 35 times of washing hair | 13.16 | 0.05 |

First, according to the present invention, the value of the difference ΔL in brightness before and after washing hair is within 3, and within 3 is hardly noticeable if they are arranged side by side, and generally within the same range of brightness. In other words, it can be seen that it is a color treatment that does not easily fade even after washing hair. In addition, the difference in L * between the coloring using only color treatment and the coloring using painter A.B.C was about 7, which was the range in which the difference in brightness could be visually recognized. In other words, it can be said that the coloring using painter A.B.C was better dyed and the hair color was darker than the coloring using only color treatment.

Further, in the present invention using the painter A, B and C alone and the painter (A+B)+C, the use of the painter A, B and C alone made the color brighter although the value of ΔL was within the range used for 1.43 color management. On the other hand, in the present invention of painter (A+B)+C, the value of ΔL was 0.05, which was in the range in which the difference in brightness could not be discriminated. In other words, the use of painter A, B and C alone caused a slight discoloration, but this case of painter (A+B)+C did not show discoloration. From this, it can be seen that the method of using the painter of the present invention is a coloring method with high dyeing power and good color retention.

That is, from these results, it is possible that the hair after dyeing may be discolored more than the discoloration caused by washing the color agent alone by simply adding the hair cosmetic and the cuticle care agent to the color agent. It can be said that after applying a mixture of the hair cosmetic and the coloring agent as in Example 3 (that is, applying the hair cosmetic and the coloring agent at the same time), the cuticle care agent is applied to the hair to reduce the discoloration of the wash.

Example 4

Furthermore, the dyed hairs of Example 3, Reference Example 3 and Reference Example 4 (without washing hair) were measured using an infrared moisture meter (model: FD-660, manufactured by Kett Science Laboratories) of a heat drying/mass measuring method. Table 9 shows the measurement results. From this result, it was found that the water content of the hair dye is increased by adding the hair cosmetic and the cuticle care agent, as compared with the case of using the hair coloring agent alone.

TABLE 9

| | Water content in hair(%) |
|---|---|
| Dyeing hair using only hair painter A | 8.6 |
| Dye hair applied in the order of painter B, A, C | 9.1 |
| Dyed hair coated with C after using a painter (mixture of A and B) | 9.1 |

From the above, it was found that, in coloring hair or the like, the strength and the water content of the hair are improved by combining the hair cosmetic and the cuticle care agent, as compared with the case of using the color agent alone. Further, it has been found that discoloration due to washing hair can be suppressed by applying a cuticle care agent after applying a mixture of a color agent and a hair cosmetic.

INDUSTRIAL APPLICABILITY

According to the present invention, it is possible to improve the color tone, to prevent hair damage, to reduce skin damage, with respect to the hair color processing which was not good in color, and the industrial utility value is high in a wide range.

The invention claimed is:

1. A hair coloring method comprising:
   a step of applying a mixture of the following (A) and (B) in a predetermined ratio:
   (A) a hair coloring agent comprising at least a basic dye, an HC dye, a second amino acid, a first cationic surfactant, a thickener, an oil agent, a first pH adjuster, and a wetting agent, wherein the hair coloring agent has a pH of 6.8 or more; and
   (B) a hair cosmetic comprising at least an alkaline agent, a first amino acid, a higher alcohol having 12 to 22 carbon atoms, a surfactant, and a thickener, wherein the hair cosmetic has a pH from 7.0 to 11.5;
   a step of providing a predetermined time after applying the mixture; and
   a step of applying a cuticle care agent after the predetermined time.

2. A hair coloring method according to claim 1, wherein the cuticle care agent includes at least one selected from sodium bromate and hydrogen peroxide, a second cationic surfactant, and a second pH adjusting agent.

3. A hair coloring method according to claim 1, wherein the method comprises a step of leaving the cuticle care agent applied for a certain period of time after application of the cuticle care agent.

4. A hair coloring method according to claim 1, wherein a formulation ratio of mixing the hair coloring agent (A) and the hair cosmetic (B) is (A)/(B)=1 to 20.

5. A hair coloring method according to claim 1, wherein the alkaline agent is at least one selected from ammonia water, ammonium carbonate, sodium carbonate, ethanolamines, ammonium hydrogen carbonate, and arginine.

6. A hair coloring method according to claim 1, wherein the first amino acid or the second amino acid is at least one selected from cysteine, arginine, lysine, or histidine.

7. A hair coloring method according to claim 1, wherein at least one of the hair coloring agent, the hair cosmetic, and the cuticle care agent contains an antibody production inhibitor.

8. A hair coloring method according to claim 1, wherein a hair is warmed in the step of providing a predetermined time after applying the mixture.

* * * * *